United States Patent
Griffith et al.

(10) Patent No.: US 6,542,777 B1
(45) Date of Patent: Apr. 1, 2003

(54) SPIRAL SHIELD FOR A FLEXIBLE HIGH-Q IMPLANTABLE INDUCTIVELY COUPLED DEVICE

(75) Inventors: Glen A. Griffith, Newbury Park, CA (US); Janusz A. Kuzma, Englewood, CO (US); Tae W. Hahn, Northridge, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 133 days.

(21) Appl. No.: 09/766,290

(22) Filed: Jan. 19, 2001

(51) Int. Cl.[7] .................................................. A61N 1/40
(52) U.S. Cl. ........................... 607/57; 607/61; 607/137; 607/33; 607/36; 607/60
(58) Field of Search .................... 607/57, 61, 137, 607/116, 32, 33, 55, 56, 36, 60; 128/899, 903; 600/25

(56) References Cited

U.S. PATENT DOCUMENTS

| | | | |
|---|---|---|---|
| 4,400,590 A | | 8/1983 | Michelson |
| 4,532,930 A | | 8/1985 | Crosby et al. |
| 4,729,366 A | * | 3/1988 | Schaefer ........................ 600/25 |
| 4,832,051 A | * | 5/1989 | Jarvik et al. ................. 607/116 |
| 4,850,962 A | * | 7/1989 | Schaefer ........................ 600/25 |
| 5,507,303 A | * | 4/1996 | Kuzma .......................... 128/899 |
| 5,549,658 A | | 8/1996 | Shannon et al. |
| 5,571,148 A | | 11/1996 | Loeb et al. |
| 5,749,912 A | | 5/1998 | Zhang et al. |
| 5,772,575 A | * | 6/1998 | Lesinski et al. ............... 600/25 |
| 5,824,022 A | | 10/1998 | Zilberman et al. |
| 5,891,183 A | | 4/1999 | Zierhofer |
| 5,991,664 A | | 11/1999 | Seligman |
| 6,067,474 A | | 5/2000 | Schulman et al. |
| 6,178,353 B1 | * | 1/2001 | Griffith et al. ................. 607/61 |
| 6,195,585 B1 | * | 2/2001 | Karunasiri et al. ............ 607/57 |
| 6,212,431 B1 | | 4/2001 | Hahn et al. |
| 6,259,951 B1 | * | 7/2001 | Kuzma et al. ................. 607/57 |
| 6,272,382 B1 | * | 8/2001 | Faltys et al. ................... 607/57 |
| 6,275,736 B1 | * | 8/2001 | Kuzma et al. ................. 607/57 |
| 6,308,101 B1 | * | 10/2001 | Faltys et al. ................... 607/57 |
| 6,321,118 B1 | * | 11/2001 | Hahn ........................... 607/61 |

FOREIGN PATENT DOCUMENTS

WO  WO-99/06108 A1  2/1999

* cited by examiner

Primary Examiner—Teresa Walberg
Assistant Examiner—Fadi H. Dahbour
(74) Attorney, Agent, or Firm—Kenneth L. Green; Bryant R. Gold

(57) ABSTRACT

A spiral shield for an implantable secondary coil confines the electrical field of the coil, and thus prevents capacitive coupling of the coil through surrounding dielectrics (such as human tissue.) Known implantable devices receive power inductively, through a secondary coil, from a primary coil in an external device. Efficient power reception requires that the coils be tuned to the same resonant frequency. Use of the spiral shield results in predictable electrical behavior of the secondary coil and permits the secondary coil to be accurately tuned to the same resonate frequency as the primary coil. To further improve performance, spacers made from SILBIONE®LSR 70 reside between turns of the coil to reduce turn to turn and turn to shield capacitances. Reducing the capacitances prevents excessive reduction of the self resonant frequency of the coil. The coil is imbedded in SILBIONE®LSR 70, allowing for a thin and flexible coil.

26 Claims, 3 Drawing Sheets

SPIRAL SHIELD FOR A FLEXIBLE HIGH-Q IMPLANTABLE INDUCTIVELY COUPLED DEVICE

BACKGROUND OF THE INVENTION

The present invention relates to the efficient transmission of power in implantable medical devices, and more particularly to an improvement to inductive coupling for Implantable Cochlear Stimulator (ICS) systems. Such implantable cochlear stimulator systems provide the sensation of hearing for the hearing impaired and the profoundly deaf. Inductive coupling serves the important function of transmitting power from an external device to the implantable device of the cochlear stimulator system. The power is transmitted from a primary coil in the external device, to a secondary coil in the implantable device. The power used in known ICS systems is provided by a battery in an external part of the system, and a larger battery is required if power is wasted. Therefore, efficient inductive coupling is essential for miniaturized systems that are under development.

U.S. Pat. No. 4,400,590 issued Aug. 23, 1983 for "Apparatus for Multi-Channel Cochlear Implant Hearing Aid System" describes and illustrates a system for electrically stimulating predetermined locations of the auditory nerve within the cochlea of the ear, which system includes a multi-channel intra-cochlear electrode array. The hearing aid system described in the '590 patent receives audio signals at a signal processor located outside the body of a hearing impaired patient. The processor converts the audio signals into analog data signals which are transmitted by a cable connection through the patient's skin to the implantable multi-channel intra-cochlear electrode array. The cable connection through the skin of the patient to the intra-cochlear electrode array is undesired in that it interferes with the freedom of movement of the patient and represents a possible source of infection.

U.S. Pat. No. 4,532,930, issued Aug. 6, 1985 for "Cochlear Implant System For an Auditory Prosthesis" describes and illustrates a multiple electrode system which does not employ a through the skin connector, and therefore avoids the problems associated with a cable passing through the skin. The '930 patent describes an inductive link between a primary coil disposed outside the body, and a secondary coil implanted within the body. U.S. Pat. No. 5,891,183 issued Apr. 6, 1999 for "Device for Transferring Electromagnetic Energy Between Primary and Secondary Coils," describes coils designed to improve the magnetic coupling between the primary and secondary coils. Different coil configurations are described and modeled in the '183 patent, and the coupling coefficients for differing coil alignments are presented. The '930 and the '183 patents are herein incorporated by reference.

U.S. Pat. No. 5,824,022 issued Oct. 20, 1998 for "Cochlear Stimulation System Employing Behind-The-Ear Speech Processor with Remote Control," describes a cochlear stimulator system with a Behind-The-Ear (BTE) speech processor. BTE speech processors offer several advantages, but because of their small size, are limited in the size of the battery they may carry (which in turn limits the useful life of the battery.) The small battery size results in a requirement for very low power consumption.

Unfortunately, in known implantable stimulation systems, the efficiency of the inductive power transmission is reduced by capacitive coupling between turns of the secondary coil and by unwanted magnetic coupling of the secondary coil with surrounding material. The capacitive coupling between turns of the secondary coil is a strong function of the surrounding materials, and the presence of a high dielectric material intensifies the electric field across the turns and terminals of the coils, adding shunt capacitance to the coil. Thus, when a coil is directly immersed in a high dielectric material, or in the proximity of a high dielectric material, such as a human body with a relative dielectric constant eighty one times that of air, the capacitive coupling between individual turns results in the self resonance frequency of the coil being substantially reduced, and the overall mutually coupled inductor circuit operation is greatly changed.

Known implantable devices position the secondary coil in close proximity to other electrical components of the implantable device, or place the secondary coil in a case which contains many of other electrical components of the implantable device. Such placement results in magnetic coupling between the secondary coil and the other electrical components, or with the case. The capacitive and magnetic coupling, plus other losses, results in only about 50% efficiency in inductive power transmission, and therefore necessitates a larger battery to meet power requirements. The need to minimize battery size results in a continuing need for greater efficiency in the inductive transfer of power to implantable medical devices.

SUMMARY OF THE INVENTION

The present invention addresses the above and other needs by providing an implantable secondary coil assembly with a spiral shield. The secondary coil assembly includes a winding with a small number of substantially round turns. The winding comprises multi-strand wire in a biocompatible polymer sheath. A spacer, made from a biocompatible polymer material, resides between adjacent turns of the coil, and between the outermost turn of the coil and the shield. The spiral shield is electrically connected to the outer turn of the winding, and is wound toroidally around the winding on both sides of the connection, with an electrical gap existing in the shield opposite the connection. A magnet that is about one third to one half the diameter of the assembly is provided at the center of the secondary coil to provide a means for holding a head piece containing a primary coil adjacent to the secondary coil. The entire assembly is preferably encapsulated in the same biocompatible polymer material used for the sheath and the spacer. In one embodiment, a balum transformer is included which connects the secondary coil to the load.

In accordance with one embodiment of the invention, a spiral shield is wound toroidally around the winding of an implantable secondary coil. The implantable secondary coil receives energy inductively transmitted from an external primary coil. Efficient inductive energy transfer requires that the primary and secondary coil be tuned to the same resonant frequency. An unshielded secondary coil, implanted directly in the human body, experiences operational frequency resonance shifts that result from dielectric loading of the implanted secondary coil. The use of a spiral shield confines the electrical fields applied to the winding, and thereby limits capacitive loading between turns. By limiting the capacitive loading, the operational frequency resonance shifts that result from capacitive loading are minimized, and the secondary coil can be accurately tuned to the resonant frequency of the primary coil, regardless of the presence or absence of other dielectric material, thus stabilizing the tuning and improving the efficiency of the inductive power transmission.

It is a feature of the present invention to provide a spacer made from a bio-compatible polymer material, which spacer is laid between adjacent turns of the secondary coil winding. The bio-compatible polymer material selected has a low dielectric constant, thus reducing turn-to-turn and turn-to-shield capacitances, and making the material an ideal coil potting material. Reducing the turn-to-turn and turn-to-shield capacitances prevents excessive reduction of the self resonant frequency of the coil which might otherwise occur.

It is another feature of the invention to use a spirally wrapped foil, solid or multi-strand wire, or wire mesh as a shield. A solid shield would result in a very stiff structure, which structure would distort or collapse when the coil assembly is flexed. The spiral wrapping provides a very flexible member, similar to a coil spring, which can easily be bent without permanent damage or distortion.

It is a further feature of the invention to encapsulate the secondary coil in a bio-compatible polymer insulation. The combination of the bio-compatible polymer encapsulation, multi-strand wire, and spiral shield, results in a thin, flexible, secondary coil assembly. Such a thin and flexible assembly easily conforms to contours of the skull at the site of an implant, may be located in tissue that experiences flexing, and resists damage from impacts. Further, the wire of the present invention is in a bio-compatible polymer sheath. As a result of employing the same bio-compatible polymer material for the encapsulation, the spacer, and the sheath, the secondary coil assembly has a uniform flex and therefore conforms uniformly to the implant location.

It is an additional feature of the encapsulation of the present invention to allow the secondary coil to be located outside a hermetically sealed metal case, or any case containing other electrical components. The presence of other electrical components in the vicinity of the secondary coil results in unwanted magnetic coupling. Such unwanted magnetic coupling reduces the efficiency of the inductive power transmission. In some embodiments, a permanent magnet is located in the center of the secondary coil as part of a headpiece retention system. In the present invention, the magnet is limited to being about one-half the diameter of the secondary coil. Advantageously, the magnetic fields from the magnet are generally confined within a region of one-half the secondary coil diameter, and centered in the secondary coil. Thus, the magnetic field from the magnet does not couple with the magnetic fields of the inductive coupling, thereby reducing losses from magnetically induced eddy currents.

It is also a feature of one embodiment of the present invention to connect a balum transformer between the secondary coil and the load, to achieve balanced operation of the coil. Balanced operation reduces by one half the voltage present between the secondary coil ends, and the case containing the implantable electronics, and provides a DC-coupled method of attaching the shield to the case. Such balanced operation reduces or eliminates problems resulting from electronic fields in the human body. The balanced configuration also connects the winding-to-shield, and winding-to-case capacitances in series, thus reducing the apparent capacitance shunting the winding. This increases the self-resonance frequency of the coil substantially, which can allow operation at higher frequencies, or alternatively, allows an increase in the number of turns in the coil for operation at a single fixed frequency. Increasing the number of turns increases the coupling between coils such that higher bandwidth, and lower losses, can be obtained.

As a result of the several improvements to the efficiency of inductive power transmission from the primary coil to the secondary coil assembly, recited above, the total power required to operate an implanted medical device from an external power source is substantially reduced. Such reduction in power requirements enables the use of a small battery in BTE hearing devices, and other applications, requiring compact implantable device systems.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
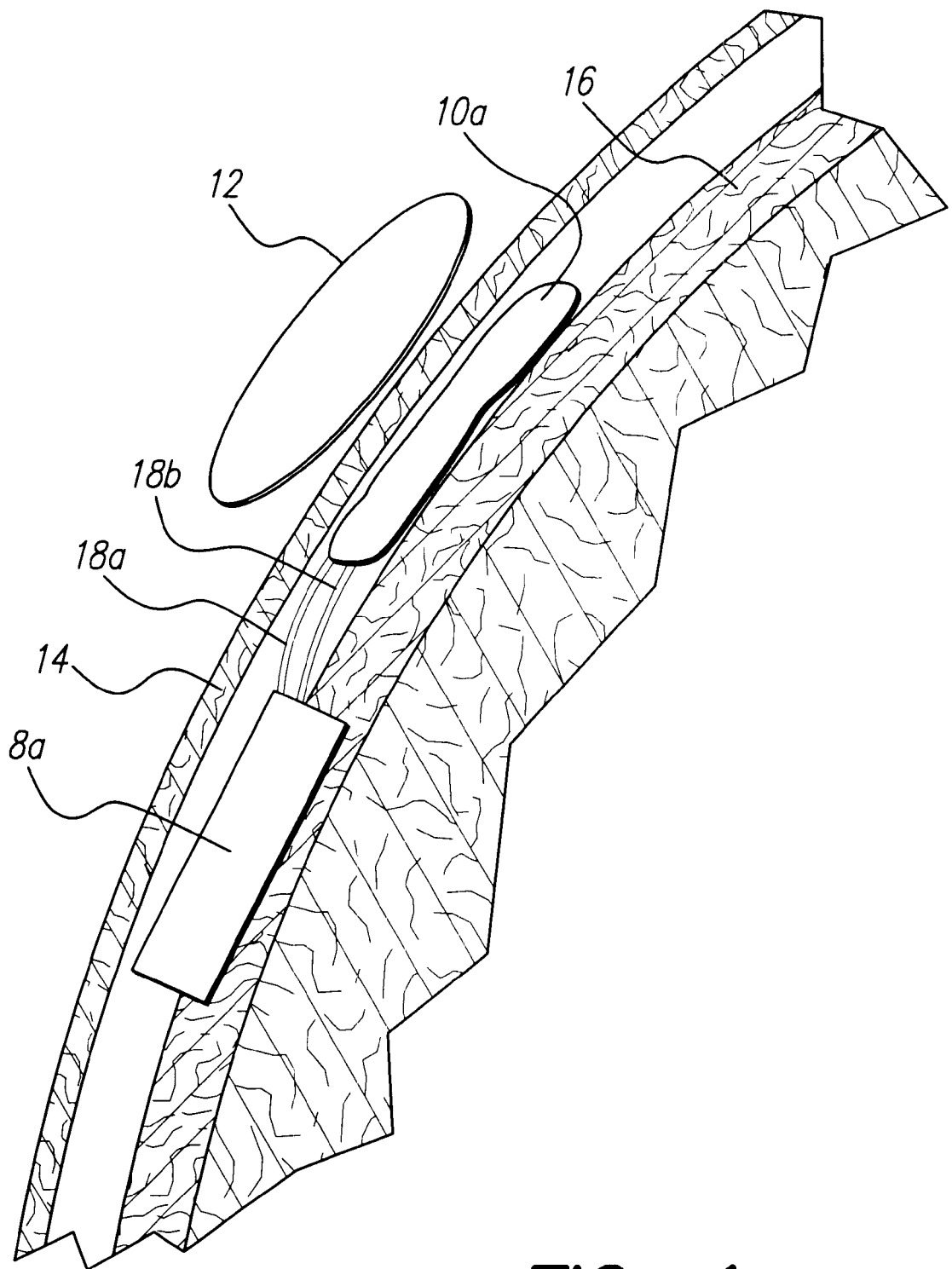
FIG. 1 depicts a secondary coil assembly implanted beneath a layer of skin and against a section of skull, with an external primary coil positioned adjacent to the secondary coil assembly.

A secondary coil assembly 10a of the present invention is shown in FIG. 1 implanted between skin 14 and skull 16 of a patient. An external primary coil 12 is shown adjacent to the secondary coil assembly 10a. Leads 18a, 18b electrically connect the secondary coil assembly 10a to an implantable device 8a of an Implantable Cochlear Stimulation (ICS) system or other implantable system. Power is provided to the implantable device 8a inductively through inductive coupling of the primary coil 12 with the secondary coil assembly 10a. The secondary coil assembly 10a resides in a thin pocket and conforms to the curvature of the skull 16. The implantable device 8a resides in a relief formed in the skull 16 during an implant procedure.

The view presented in FIG. 1 represents an application of the present invention wherein the flexibility of the secondary coil assembly 10a allows the secondary coil assembly to conform to the contour of the skull. Those skilled in the art will recognize other advantageous applications of a flexible secondary coil assembly. These other applications include implanting the secondary coil assembly in locations subject to impacts wherein a ridged secondary coil assembly is likely to be damaged. Another application is in a location where the surrounding tissue experiences movement, and a stiff secondary coil assembly is likely to cause discomfort or tissue damage. These and other applications will be apparent to those skilled in the art, and are intended to come within the scope of the present invention.

Figure 2:
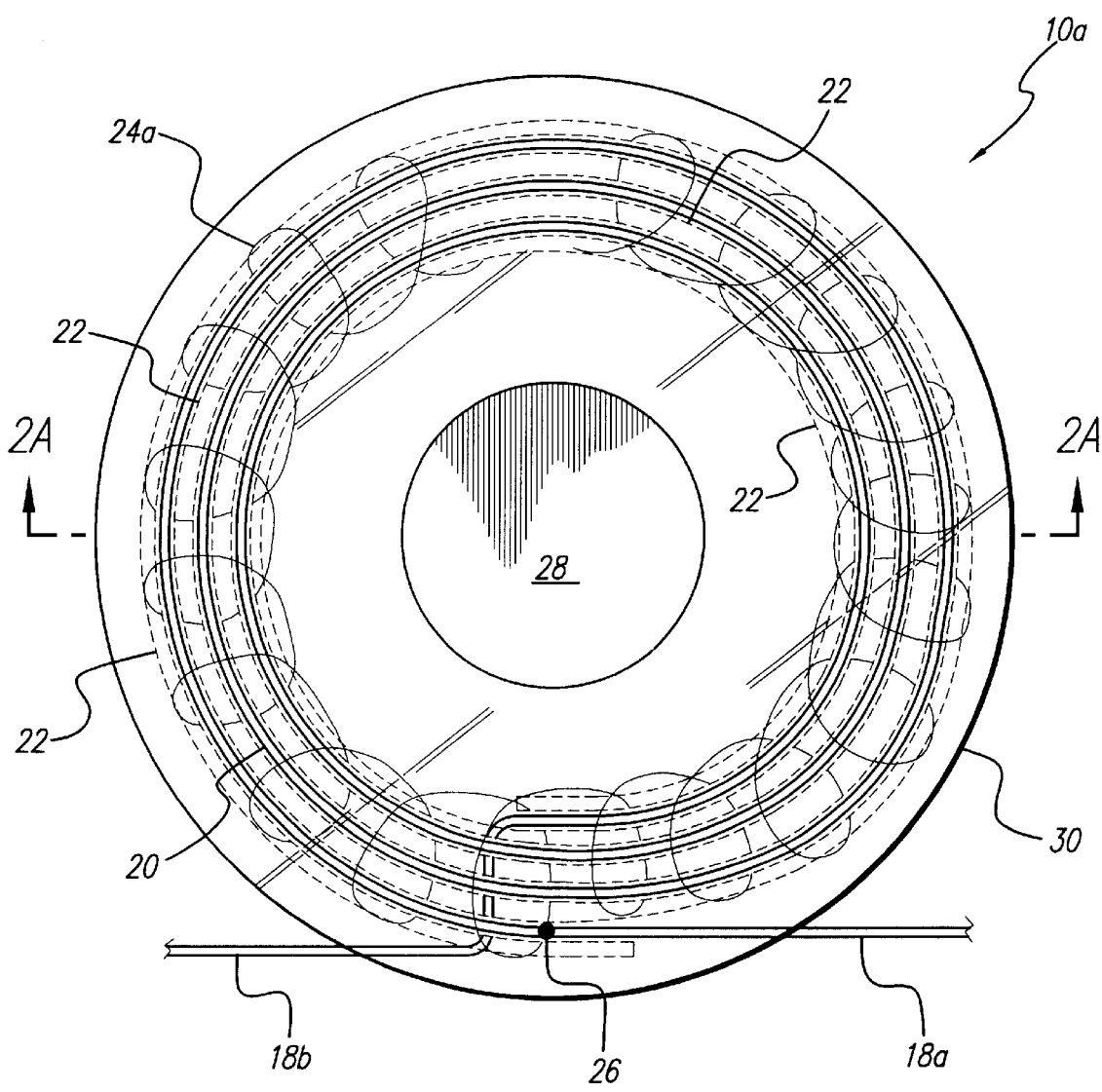
FIG. 2 shows the details of the secondary coil assembly.

A detailed view of the secondary coil assembly 10a is shown in FIG. 2. The secondary coil assembly 10a includes a winding 20 that inductively couples with the primary coil 12 to receive power transmitted to the secondary coil assembly 10a. In a preferred embodiment, the winding 20 comprise about 3 turns of a multi-stranded wire with a gap between the surfaces of the multi-strand wire of adjacent turns of at least the diameter of the multi-stranded wire. A first shield 24a is wound toroidally around the winding 20 and is separated from the surface of the nearest of the multi-strand wire of the winding 20 by at lease one diameter of the multi-stranded wire. A spacer 22, represented by a heavy dashed line in FIG. 2, resides between adjacent turns of the winding 20, and between the inner-most turn of the winding 20 and the shield 24a, and between the outer-most turn of the winding 20 and the shield 24a. The shield 24a is connected to the outer-most turn of the winding 20 at a connection 26, and is wound toroidally around the winding 20 to each side of the connection 26. In one embodiment the spiral shield 24a is formed from a metal ribbon about 0.002 inches thick, and about 0.010 to 0.015 inches wide, and the spiral shield 24a is wound to leave a gap between adjacent turns of the metal ribbon about equal to the width of the metal ribbon. Such ribbon shielding provides a good compromise between the effectiveness of the electrical shielding and flexibility. In a second embodiment, the spiral shield 24a is formed from about forty to one hundred winds of either a solid wire about 0.1 mm in diameter, or a multi-stranded wire of about seven strands of about 25 micron wire. A spiral shield 24a made from such solid or stranded wire offers increased flexibility compared to a spiral shield formed from a metal ribbon. In a third embodiment, a spiral shield 24a is made wire mesh with a suitable number of winds to shield the winding 20. In each embodiment of the spiral shield 24a, there is an electrical gap in the shield 24a opposite the connection 26 to prevent current from flowing in the spiral shield 24a. The winding 20, spacer 22, and spiral shield 24a are encapsulated in a bio-compatible polymer, low dielectric material, such as SILASTIC® or SILBIONE®LSR 70, encapsulation 30. The spacer 22, and a sheath for the multi-strand wire, may be made from the same material as the encapsulation 30, or alternatively may be made from any suitable material with similar physical characteristics. A magnet 28 resides in the center of the encapsulation 30 and is about one third to one half the diameter of the encapsulation 30. Leads 18a, 18b electrically connect the secondary coil assembly 10a to the implantable device 8a.

The overall diameter of the secondary coil assembly 10a shown in FIG. 2 is about one inch, but the diameter may vary based upon the carrier frequency of the transmission, and upon limitations imposed by requirements to fit a specific application. Applications of secondary coil assemblies to implantable medical devices other than cochlear implants, which secondary coil assemblies include a spiral shield around the secondary coil winding, are also intended to come within the scope of the present invention.

The secondary coil assembly 10a shown in FIG. 2 appears as a flat spiral coil for purposes of making a simple drawing. The winding 20 may be in various configurations without departing from the scope of the present invention. While the winding 20 comprise about 3 turns, the actual number of turns may vary depending upon other parameters, for example, frequency. Further, the secondary coil assembly 10a is a flexible structure and does not define a single shape. A variety of winding configurations that may be encapsulated in a flexible material, and shielded as taught herein, are contemplated. These various other embodiments of a flexible shielded secondary coil are intended to come within the scope of the present invention.

Figure 2A:
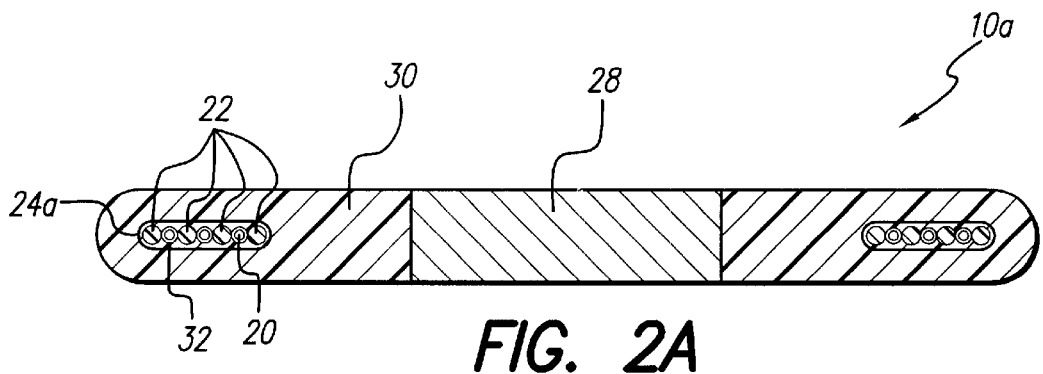
FIG. 2A shows a cross-sectional view of the secondary coil assembly taken along line 2A—2A of FIG. 2.

A cross-sectional view of the secondary coil assembly 10a, taken along line 2A—2A of FIG. 2 is shown in FIG. 2A. The sectional view shows the arrangement of the winding 20, spacer 22, and magnet 28 in the encapsulation material 30. Additionally, a sheath 32 is shown surrounding the individual multi-strand wires of the winding 20. The sheath 32 is made from either the same material as the encapsulation 30, or a material with similar physical characteristics (i.e. a bio-compatible polymer, low dielectric material such as SILASTIC® or SILBIONE®LSR 70.) The relative sizes and spacing of the turns of the winding 20 and spacer 22 are not shown to scale, and in a preferred embodiment are closer together and nearer to the outside perimeter of the encapsulation 30. As stated above, flat spiral winding is one of many embodiments of the present invention, and the arrangement of winding in FIG. 2A is for illustration of a single embodiment. Further, while the encapsulation 30 in FIG. 2A is shown as a flat disk, the encapsulation 30 is flexible with the ability to take on a variety of shapes.

Figure 3A:
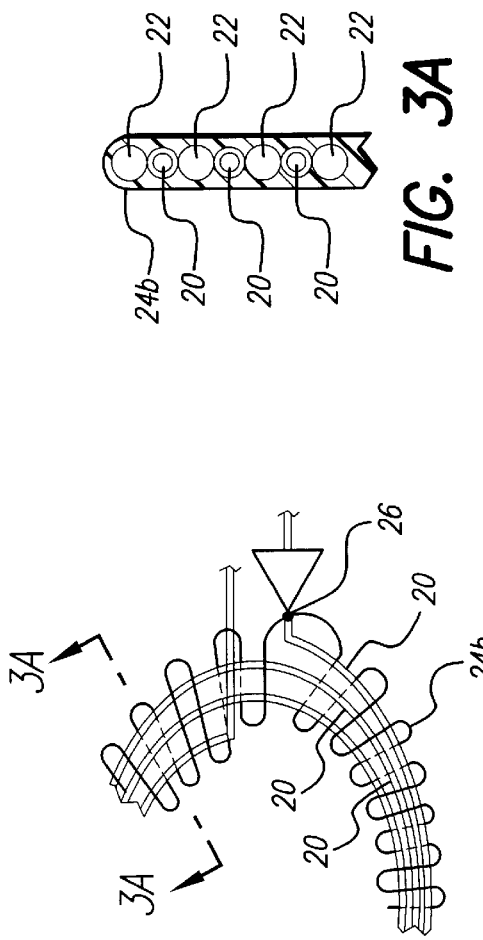
FIG. 3A shows a cross-sectional view of the second shield taken at line 3A—3A of FIG. 3.
Figure 3:
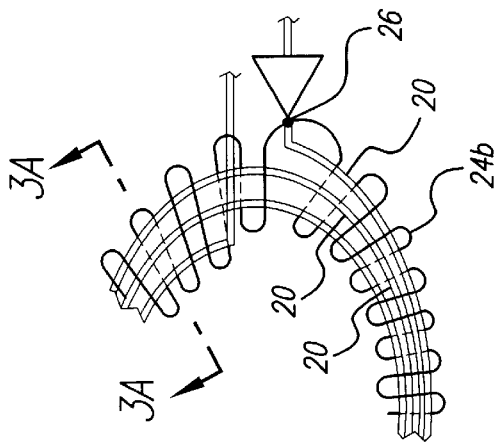
FIG. 3 shows a partial view of a secondary coil assembly with a second shield that reaches alternatively to the right side of the winding and then to the left side of the winding.

An alternative shield 24b is shown in FIG. 3. The shield 24b is not wound toroidally around the winding 20, but instead the shield 24b reaches alternatively to one side of the winding 20, and then reverses and reaches over the winding 20 and to the opposite side of the winding 20, without circling the winding 20. The view provided shows only one section of the secondary coil. A cross-sectional view of the shield 24b, taken at line 3A—3A of FIG. 3 is shown in FIG. 3A. The shield 24b is shown running along each side of the winding 20, and reaching over the winding 20, but not crossing under the winding 20. The use of "over" and "top" in this description refer to the outer radius of the winding 20.

Figure 4:
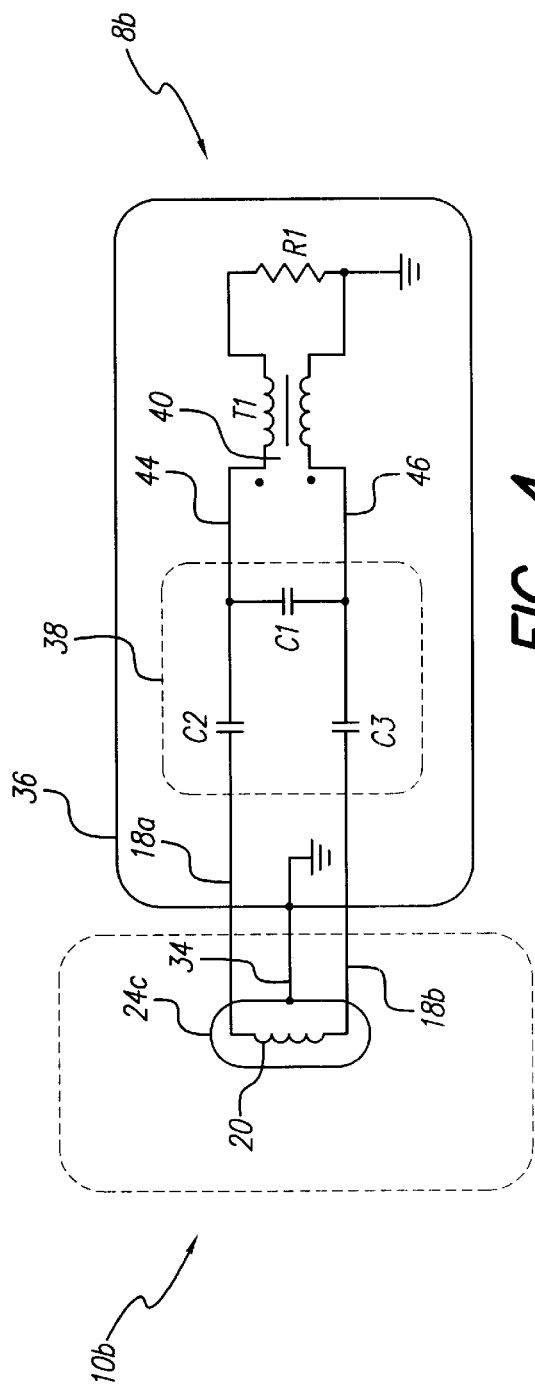
FIG. 4 schematically depicts a second embodiment of a secondary coil assembly which is connected to a balum transformer.

A second secondary coil assembly 10b is shown in FIG. 4. The secondary coil assembly 10b is connected to a second implantable device 8b, which device contains electronic circuitry for performing a desired function. The implantable device 8b includes a conductive case 36. A third spiral shield 24c is wound toroidally around the winding 20, and is electrically grounded to the conductive case 36. The implantable device 8b further includes a balum transformer T1 in order to achieve balanced operation of the secondary coil assembly 10b. The secondary coil assembly 10b is connected to the balum transformer T1 through an impedance matching network 38. The lead 18a is connected to a first side 40 of the balum transformer through a capacitor C2 and a lead 44. The lead 18b is connected to the first side 40 of the balum transformer through a capacitor C3 and a lead 46. A capacitor C1 bridging the leads 44 and 46 between the capacitors C2 and C3, and the first side of the balum transformer T1. A second side of the balum transformer T1 is shown connected to a resistor R1. The resistor R1 represents a load equivalent to the remaining electronics of an ICS or other system.

While the invention herein disclosed has been described by means of specific embodiments and applications thereof, numerous modifications and variations could be made thereto by those skilled in the art without departing from the scope of the invention set forth in the claims.

What is claimed is:

1. An improved secondary coil assembly for inductive power reception, the secondary coil assembly comprising:
   a winding comprising a plurality of turns;
   a shield wound around the winding; and
   encapsulation comprising a bio-compatible, polymer, low dielectric material;

wherein the shield and winding reside in the encapsulation, and wherein the shield shields the winding.

2. The secondary coil assembly of claim 1 wherein the secondary coil assembly is part of an implanted part of an Implantable Cochlear Stimulation (ICS) system, and wherein operating power for the implanted part of the ICS system is inductively transmitted to the secondary coil assembly.

3. The secondary coil assembly of claim 1 wherein the secondary coil assembly is flexible and conforms to the contours of an implant site.

4. The secondary coil assembly of claim 3 wherein a permanent magnet is molded into the center of the bio-compatible, polymer, low dielectric material.

5. The secondary coil assembly of claim 4 wherein the magnet has a diameter (or a maximum linear dimension) that is about one third to one half the diameter of the secondary coil assembly.

6. The secondary coil assembly of claim 3 wherein the implant site is against the skull of a patient, and wherein the secondary coil assembly conforms to the contours of the skull.

7. The secondary coil assembly of claim 1 wherein the turns are formed from a multi-stranded wire in a sheath made of a bio-compatible, polymer, low dielectric material.

8. The secondary coil assembly of claim 1 wherein a spacer made of a bio-compatible, polymer, low dielectric material resides between the turns, wherein the spacer separates the turns, and separates the inner-most turn from the shield, and separates the outer-most turn from the shield.

9. The secondary coil assembly of claim 1 wherein the shield is electrically connected to the outermost turn of the winding by a connection.

10. The secondary coil assembly of claim 9 wherein the shield is a spiral shield toroidally wound around the winding on both sides of the connection, and there is an electrical gap in the spiral shield opposite the connection.

11. The secondary coil assembly of claim 9 wherein the shield comprises an alternating pattern, wherein the alternating pattern reaches alternatively to one side of the winding, and then reverses and reaches over the winding to the opposite side of the winding, as the shield progresses around the circumference of the winding, and wherein the shield extends from both sides of the connection, and there is an electrical gap in the shield opposite the connection.

12. The secondary coil assembly of claim 1 further including a balum transformer, wherein the balum transformer is electrically connected between the winding and a load.

13. The secondary coil assembly of claim 1 wherein:
the winding is encapsulated in SILBIONE®LSR 70, and wherein the secondary coil assembly is flexible and conforms to the contours of an implant site;
magnet is molded into the center of the SILBIONE®LSR 70;
the turns are formed from a multi-stranded wire in a sheath made of the SILBIONE®LSR 70; and
a spacer made of the SILBIONE®LSR 70 resides between adjacent turns, wherein the spacer separates the turns, and separates the inner-most turn from the shield, and separates the outer-most turn from the shield.

14. A method for constructing a shielded and flexible secondary coil assembly comprising:
forming a winding comprising turns;
winding a spiral shield toroidally around the winding;
encapsulating the winding and spiral shield in a first bio-compatible, polymer, low dielectric material;
connecting the winding to an electrical device.

15. The method of claim 14 wherein connecting the winding to an electrical device comprises connecting the winding to the implantable part of an Implantable Cochlear Stimulation (ICS) system.

16. The method of claim 14 wherein forming a winding comprises forming the winding from multi-stranded wire, wherein the multi-stranded wire resides in a sheath made from a second bio-compatible, polymer, low dielectric material.

17. The method of claim 14 further including laying a spacer between the turns, wherein the spacer is made from a third bio-compatible, polymer, low dielectric material.

18. The method of claim 14 wherein encapsulating the winding and spiral shield includes encapsulating a magnet in the center of the secondary coil assembly, wherein the magnet is about one third to one half the diameter of the secondary coil assembly.

19. The method of claim 14 wherein encapsulating the winding and spiral shield in a first bio-compatible, polymer, low dielectric material comprises encapsulating the winding and spiral shield in SILBIONE®LSR 70.

20. The method of claim 14 wherein connecting the winding to an electrical device comprises connecting the winding to a balum transformer and connecting the balum transformer to a load.

21. A secondary coil assembly for inductive power reception for an Implantable Cochlear Stimulation (ICS) system, comprising:
a winding comprising a plurality of turns of a multi-stranded wire in a sheath;
a spacer residing between the turns;
a spiral shield toroidally wound around the winding; and
encapsulation made from a bio-compatible, polymer, low dielectric material, wherein the spiral shield, the spacer, and the winding reside in the encapsulation.

22. The assembly of claim 21 wherein the bio-compatible, polymer, low dielectric material is SILBIONE®LSR 70.

23. The assembly of claim 21 wherein a permanent magnet resides in the center of the assembly.

24. A secondary coil assembly for inductive power reception for an Implantable Cochlear Stimulation (ICS) system, comprising:
a winding comprising a plurality of turns of a multi-strand wire in a sheath;
a spacer residing between the turns;
a shield, wherein the shield comprises an alternating pattern wherein the alternating pattern reaches alternatively to one side of the winding, and then reverses and reaches over the winding to the opposite side of the winding, as the shield progresses around the circumference of the winding; and
encapsulation comprising a bio-compatible, polymer, low dielectric material, wherein the shield, the spacer, and winding reside in the encapsulation.

25. The assembly of claim 24 wherein the bio-compatible, polymer, low dielectric material is SILBIONE®LSR 70.

26. The assembly of claim 24 wherein a permanent magnet resides in the center of the assembly.

* * * * *